United States Patent [19]

Vito et al.

[11] Patent Number: 4,602,627
[45] Date of Patent: Jul. 29, 1986

[54] CABLE CONTROLLED ORTHOPEDIC LEG BRACE

[75] Inventors: Raymond P. Vito, Atlanta; H. Russell Boehm, Forrest Park, both of Ga.

[73] Assignee: Georgia Tech Research Corporation, Atlanta, Ga.

[21] Appl. No.: 647,795

[22] Filed: Sep. 6, 1984

[51] Int. Cl.⁴ ............................................. A61F 3/00
[52] U.S. Cl. ................................... 128/80 F; 128/88; 128/80 C; 623/39
[58] Field of Search ................. 128/80 R, 80 C, 80 F, 128/88; 3/1.91, 1.911, 2, 21, 22; 623/38, 39, 27, 18, 20

[56] References Cited

U.S. PATENT DOCUMENTS

| | | | |
|---|---|---|---|
| 2,107,095 | 2/1938 | Wagner | 128/80 R |
| 2,558,986 | 7/1951 | Seelert | 128/80 F |
| 2,573,866 | 11/1951 | Murphy | 128/80 F |
| 2,632,440 | 3/1953 | Hauser, et al. | 128/80 F |
| 2,772,674 | 12/1956 | Swiech et al. | 128/80 F |
| 2,883,982 | 4/1959 | Rainey | 128/80 F |
| 2,949,111 | 8/1960 | Ruotoistenmaki | 128/80 E |
| 3,230,952 | 1/1966 | Terron | 128/80 R |
| 3,552,786 | 1/1971 | Schmid | 3/22 X |
| 3,557,782 | 1/1971 | Wafer | 128/80 R |
| 3,575,166 | 4/1971 | Rosman et al. | 128/80 R |
| 3,826,251 | 7/1974 | Ross | 128/80 F |
| 3,928,872 | 12/1975 | Johnson | 128/80 CX |
| 4,289,122 | 9/1981 | Mason et al. | 128/80 E |
| 4,353,361 | 10/1982 | Foster | 128/80 C |
| 4,361,142 | 11/1982 | Lewis et al. | 128/80 C |
| 4,433,679 | 2/1984 | Mauldin et al. | 128/80 F |
| 4,450,832 | 5/1984 | Waddell | 128/80 CX |

FOREIGN PATENT DOCUMENTS

| | | | |
|---|---|---|---|
| 2152408 | 4/1973 | Fed. Rep. of Germany | 3/22 |
| 2088724 | 6/1982 | United Kingdom | 3/1.911 |

Primary Examiner—Clifford D. Crowder
Attorney, Agent, or Firm—Newton, Hopkins & Ormsby

[57] ABSTRACT

The modular components of an orthopedic leg brace assembly are strung together in bead-like fashion on a flexible cable arrangement and the components are removable so that they may be unstrung and replaced for repair or for replacement with longer components to accommodate for a user's growth. The components include an ankle-foot orthosis and upwardly extending side braces of stanchion form with an upper securing strap arrangement for securely surrounding a user's lower leg, a second pair of side braces of stanchion form with an upper securing strap arrangement for securely surrounding a user's thigh, and knee joint assemblies joining the ends of the braces to simulate the normal action of a user's knee during flexion and extension of the leg. The flexible cable arrangement allows the user to rigidly hold the entire unit in aligned, fixed relation when the leg is extended.

12 Claims, 18 Drawing Figures

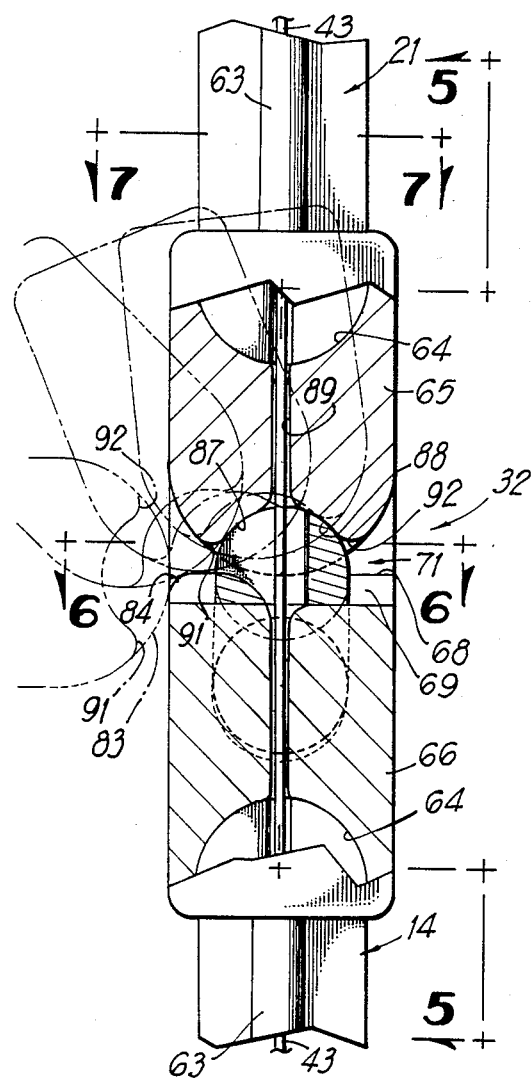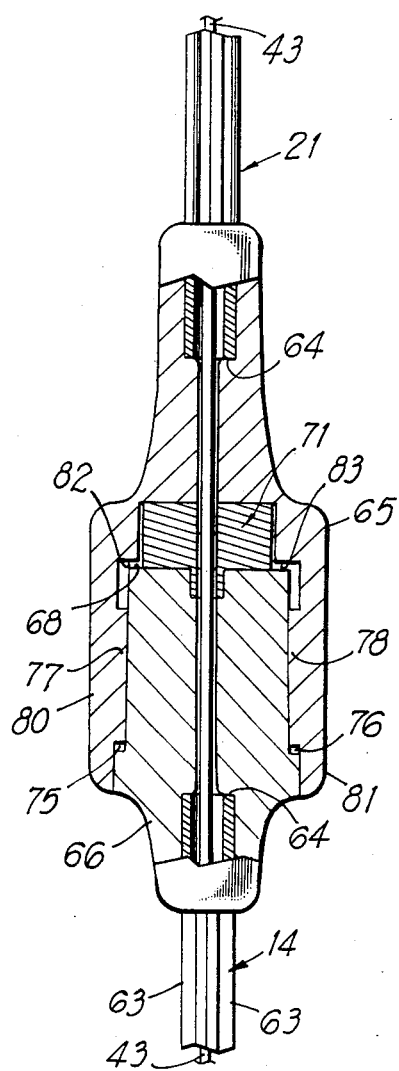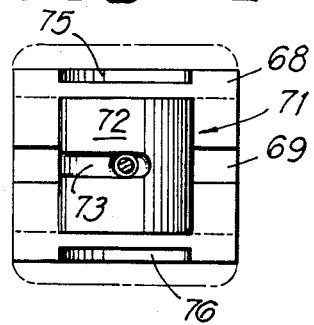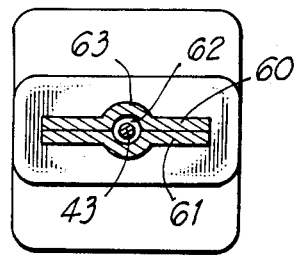

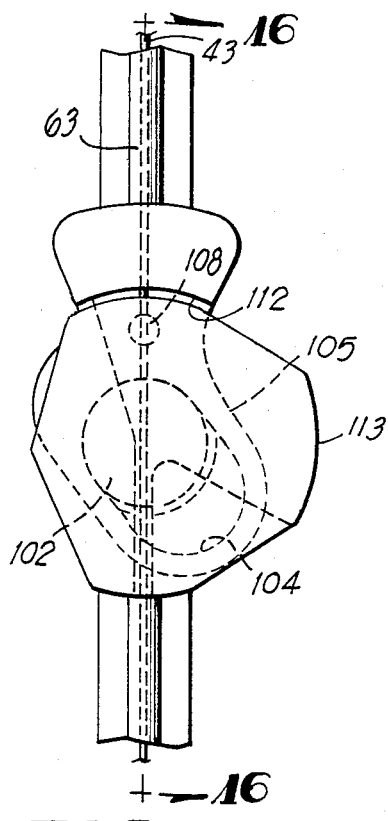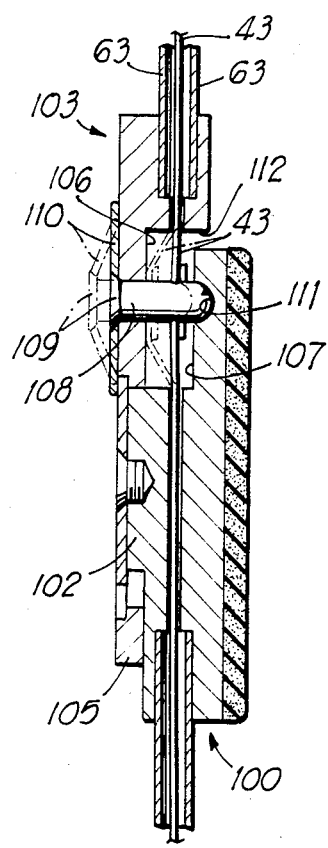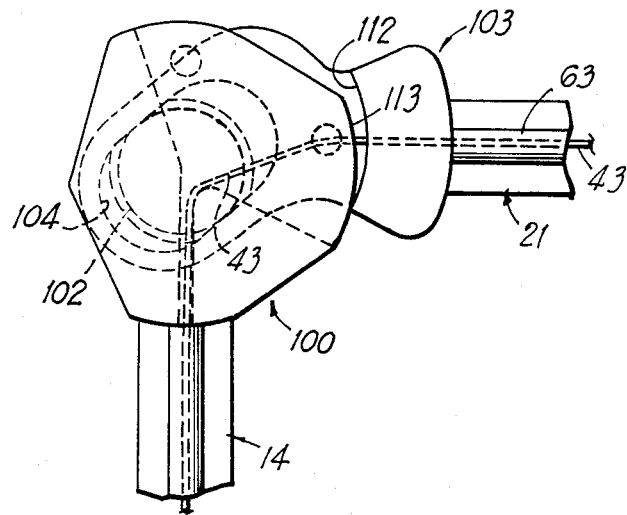
FIG 14
FIG 16
FIG 15

CABLE CONTROLLED ORTHOPEDIC LEG BRACE

BACKGROUND OF THE INVENTION

The invention relates to orthopedic leg braces and especially those which brace the upper and the lower portions of a user's leg and which incorporate a knee joint assembly. Attention is called to the following patents:

| | | |
|---|---|---|
| 4,361,142 | 11/30/82 | Lewis et al |
| 4,289,122 | 9/15/81 | Mason et al |
| 3,826,251 | 7/30/74 | Ross |
| 3,575,166 | 4/20/71 | Rosman et al |
| 3,557,782 | 1/26/71 | Wafer |
| 3,552,786 | 5/12/69 | Schmid |
| 3,230,952 | 1.25/66 | Terron |
| 2,949,111 | 8/16/60 | Ruotoistenmaki |
| 2,107,095 | 2/1/38 | Wagner |

It is well known, as is extensively discussed in the Lewis et al patent, for example, that there is particular difficulty in providing knee orthoses which provide stability while duplicating or accommodating the complex actions of a normal knee during flexion and extension.

The long term need for a leg or leg braces stems from loss of neuro-muscular control and it is particularly for such long term use that the invention is useful. For stability or bracing, the bracing is required to be secured firmly to the leg both below and above the knee and with the knee joint intervening between the bracings. If the knee joint is not effective to duplicate the compound, complex actions of a normal knee, not only is needless reaction imposed upon the user's knee during flexion and extension, but the tendency for relative movement between the firmly secured bracings and the user's leg is also a certainty. The former may well be injurious to the user and the latter results in proclivity to chafing, soreness or the like.

BRIEF SUMMARY OF THE INVENTION

It is, therefore, of concern to provide a knee orthosis which overcomes the above problems. At the same time, it is desired that the device be particularly suited for long term use and, to that end, it is of light weight and is simple to remove and replace by the user without the need for assistance. Moreover, the unit is modular so that it is easily modified from time-to-time to accommodate for the user's growth. At the same time, the device is not bulky and for that reason may be worn beneath normal clothing so as to be relatively unobtrusive. This is important particularly for children, although its benefit should not be disregarded for all classes of potential users.

Although the invention in its most fundamental form is especially applicable as a knee orthosis, the addition of upper thigh and hip bracings, united by a hip joint, is also within the scope of the invention.

Of basic concern is the utilization of upper and lower bracing elements, firmly secured to the user's leg respectively above and below the knee, knee joint means carried by the respective bracing elements and interengaged to duplicate or at least approximate for the compound, complex actions of a normal knee, a flexible tension member, and means for variably altering the tension imparted to the tension member so that, with increased tension, the entire structure tends to become a rigid and aligned unit particularly useful when the leg is extended and, wth diminished tension, the structure is easily flexed at the knee joint to duplicate or accommodate the compound, complex actions of a normal knee.

In a preferred embodiment, a pair of lower brace members are united to lie along the inner and outer sides of a user's leg and are provided with securing means for firmly anchoring them to the lower portion of a user's leg. A pair of upper brace members likewise are united and are provided with securing means for firmly anchoring them to the user's thigh. The upper and lower brace members have proximal ends which are joined by knee joint means which allows pivotal and sliding movement so that as a user's leg is flexed or extended, the normal action of a human knee is accommodated. A user actuated tensioning means is employed to frictionally engage elements of the knee joint means so as to form a rigid brace between upper and lower members when the user's leg is extended and a locking device may additionally be provided, responsive to the tensioning means, to effect a positive locking action. In this preferred embodiment, part of the uniting means for the lower brace members may be in the form of an ankle-foot orthosis.

The tensioning means includes a flexible member such as a cable and which preferably acts to string some of the elements together in bead-like fashion. This allows the brace assembly to be of very compact form so that it may be worn beneath a user's clothing, while at the same time permitting the novel knee movement simulation and rigid bracing action. It also allows the aforesaid ease of modification from time-to-time to accommodate for the user's growth, i.e., it is of modular form.

These and other objects of the invention will become apparent as the following Description proceeds.

BRIEF DESCRIPTION OF THE DRAWING FIGURES

FIG. 4 is a partial section of the knee joint illustrated in FIG. 3;

FIG. 5 is a partial section as indicated by section line 5—5 in FIG. 4;

FIG. 6 is a horizontal section as indicated by section line 6—6 in FIG. 4;

FIG. 7 is a horizontal section through one of the base members as indicated by section line 7—7 in FIG. 4;

FIG. 14 is an elevation of upper and lower brace members connected by the modified knee joint;

FIG. 15 is a view similar to FIG. 14 but showing the modified knee joint in flexed position;

FIG. 16 is a vertical section taken along section line 16—16 in FIG. 15;

DETAILED DESCRIPTION OF THE INVENTION

Figure 1:
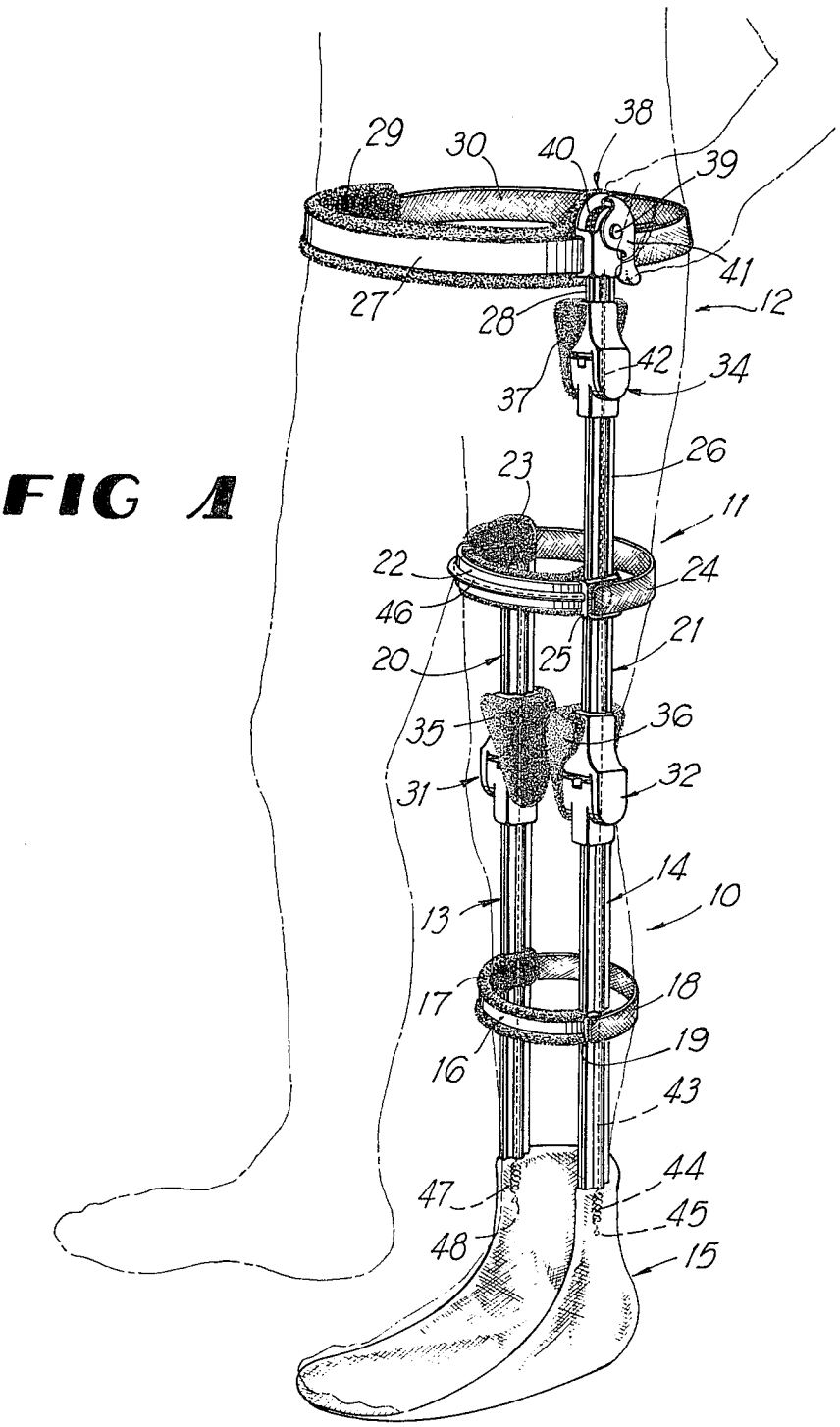
FIG. 1 is a perspective view of one embodiment of the invention.

With reference to FIG. 1, one form of the invention is illustrated therein and in this configuration it will be seen to include a lower leg assembly indicated generally by the reference character 10, an upper leg or thigh assembly indicated generally by the reference character 11, and a hip assembly indicated generally by the reference character 12. The lower assembly 10 comprises a pair of rigid, elongate side braces 13 and 14 which, in the embodiment shown, are associated with an ankle-foot orthosis indicated generally by the reference character 15. These two members 13 and 14 are rigidly interconnected by an arch-like brace or rigidifying member 16 provided with suitable padding material 17 which overlaps on the inner side of the members 13 and 14 as well and there is provided a securing means in the form of a strap 18 of flexible material such as cloth or the like and provided with a Velcro fastening joint as indicated by the reference character 19 or with other means for joining. The orthosis 15 has the lower ends of the members 13 and 14 embedded therein and thus functions, together with the member 16 to unite the brace members 13 and 14 rigidly so that they are adapted to lie alongside inner and outer sides of the user's leg from the ankle and foot region to the region of the knee.

The upper assembly 11 includes the inner side member 20 and the outer side member 21 which are rigidly united by the arch-like member 22 which is provided, as is the case for the member 16 with the padding 23 overlapping the inner sides of the members 20 and 21 as shown. Also associated with these two members 20 and 21 is the securing means in the form of a flexible strap 24 again provided with a Velcro joint at 25. In this embodiment of the invention, the upper member 21 is extended as indicated by the reference character 26 to terminate in the region of the user's hip joint. A waistband member comprising a rigid arch-like construction 27 carries a short brace element or member 28 and is also provided with interior padding as at 29 and has associated with it a flexible strap 30 also having a Velcro type fastening.

As thus far described, it will be appreciated that the two members 13 and 14 which form the lower brace mechanism and the upper brace member 20 and 21 are more or less in alignment with each other when the user's leg is extended as is shown in FIG. 1 and the proximal ends of these members 13,20 and 14,21 are pivotally and slidably interconnected by the knee joint means indicated generally by the reference characters 31 and 32, the details of which will be presently described. Likewise, the extension 26 and the short brace member 28 are joined by hip joint mechanism indicated generally by the reference character 34 which establishes a pivotal connection between these members, there being no necessity for the sliding connection which characterizes the knee joint means 31,32. It will be readily apparent that the orthopedic device shown in FIG. 1 may be easily removed and replaced by the user simply by disconnecting the straps 18, 24 and 30 or restrapping them in place. For added comfort, the knee joint means 31 and 32 have padding 35 and 36 associated therewith and the hip joint 34 likewise has padding 37, substantially as is shown.

In addition to the components generally described above, the rigid waistband 27 carries a pawl and ratchet assembly indicated generally by the reference character 38, the pivotal axis of which is indicated at the reference character 39 for rotatably receiving the ratchet wheel 40 and the operating lever 41 thereof. The pawl (not shown) is accessible and releasable by the user, as is the lever 41. The purpose of this mechanism is to allow the user to manipulate the tensioning means which is a characteristic of this invention. In the embodiment shown, the tensioning means includes an upper flexible tension member or cable 42 and a lower flexible tension member or cable 43. One end of the cable 43 is connected to a tension spring 44 which is anchored at 45 to the lower end of the brace member 14 and the cable 43 extends upwardly within a channel of the member 14, through the knee joint means 32, through the upper member 21 and then in crossing over relation within the channel or bead 46 of the arch-like member 22 and thence downwardly within the member 20, through the knee joint means 31, and through the member 13 to connect to a further tension spring 47 which is anchored at 48 to the lower end of the member 13. The cable 42 is connected to the cable 43 by means of a suitable ring or loop so that when the pawl and ratchet mechanism 38 is operated to tension the cable against the springs 44 and 47, components of the several joints 31, 32 and 34 will be frictionally engaged so as to at least resist pivotal motions thereat and effectively function as a rigid orthopedic brace unit for the user's leg and hip in the particular embodiment shown. By releasing or relaxing the tension, the user may then allow normal pivotal motions of the knee joint means 31 and 32 and of the hip joint 34 so as to allow easy motion of the hip joint as well as the knee joint.

Figure 17:
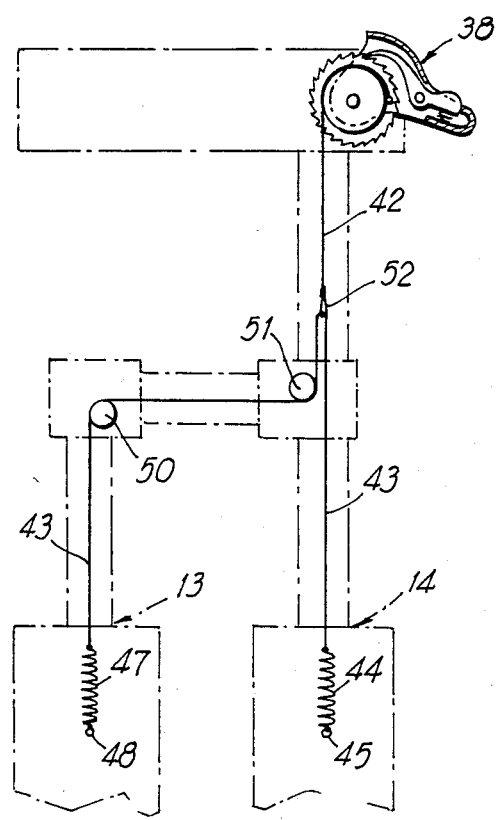
FIG. 17 is a diagrammatic view illustrating one form of tensioning means.

To facilitate an understanding of the cable arrangement shown in FIG. 1, reference is had to FIG. 17. From FIG. 17, it will be appreciated that at those points where the cable 43 must be directed substantially through right angles, suitable guide elements 50 and 51 may be employed. FIG. 17 also shows the ring or loop 52 which connects the upper cable 42 to the lower cable 43, the purpose of the loop or ring connection at 52 being to allow the cable 43 to be tensioned evenly throughout its length so as to impose the same frictional interengaging force at both of the knee joint means 31 and 32.

Figure 18:
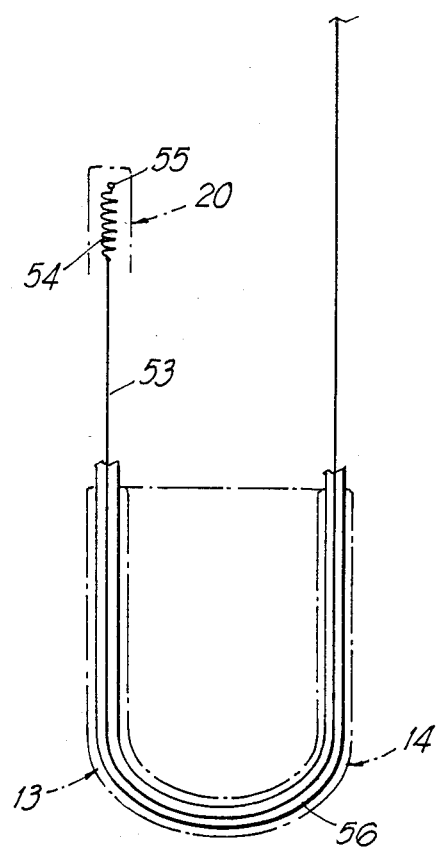
FIG. 18 is a diagrammatic view illustrating another form of tensioning means.

An alternative cable construction employing but a single cable is shown in FIG. 18. In this case, the single length of cable 53 is connected to one end of the tension spring 54 which is pin connected at 55 to the upper end of the member 20 and passes beneath the user's foot within the foot orthosis 15 through any suitable guiding mechanism 56 which may, if desired, be formed as extensions of the lower ends of the members 13 and 14, and thence upwardly for connection ultimately to the pawl and ratchet mechanism which is not illustrated in FIG. 18.

Referring at this time more particularly to FIGS. 2–7 wherein one of the knee joint means is shown, it will be noted first of all from FIG. 7 that the brace members are formed as two halves in this embodiment, preferably metal halves of aluminum or other materials, one of which is indicated by the reference character 60 and the other by the reference character 61. The side flanges of these halves are spot welded or otherwise suitably secured together and it will be noted that their intermediate portions define a longitudinal channel 62 by virtue of the bead formations 63 formed on each half. These channels 62 receive the flexible tension member such as the cable 43, substantially as is shown.

As can be seen from FIG. 4, the ends of the brace members are rounded as is indicated at reference characters 64 and the two main components 65 and 66 of the two knee joint assemblies 31,32 are recessed correspondingly to receive these ends in slip-fitted relationship therewithin, see also FIG. 5. This relationship is extremely useful when the orthopedic device is fitted to a growing person such as a child inasmuch as it will be readily apparent that at time intervals such as are indicated by growth, a new orthopedic device may be fabricated simply by replacing the various brace elements with slightly longer ones to accommodate for that growth.

Figures 2, 3:
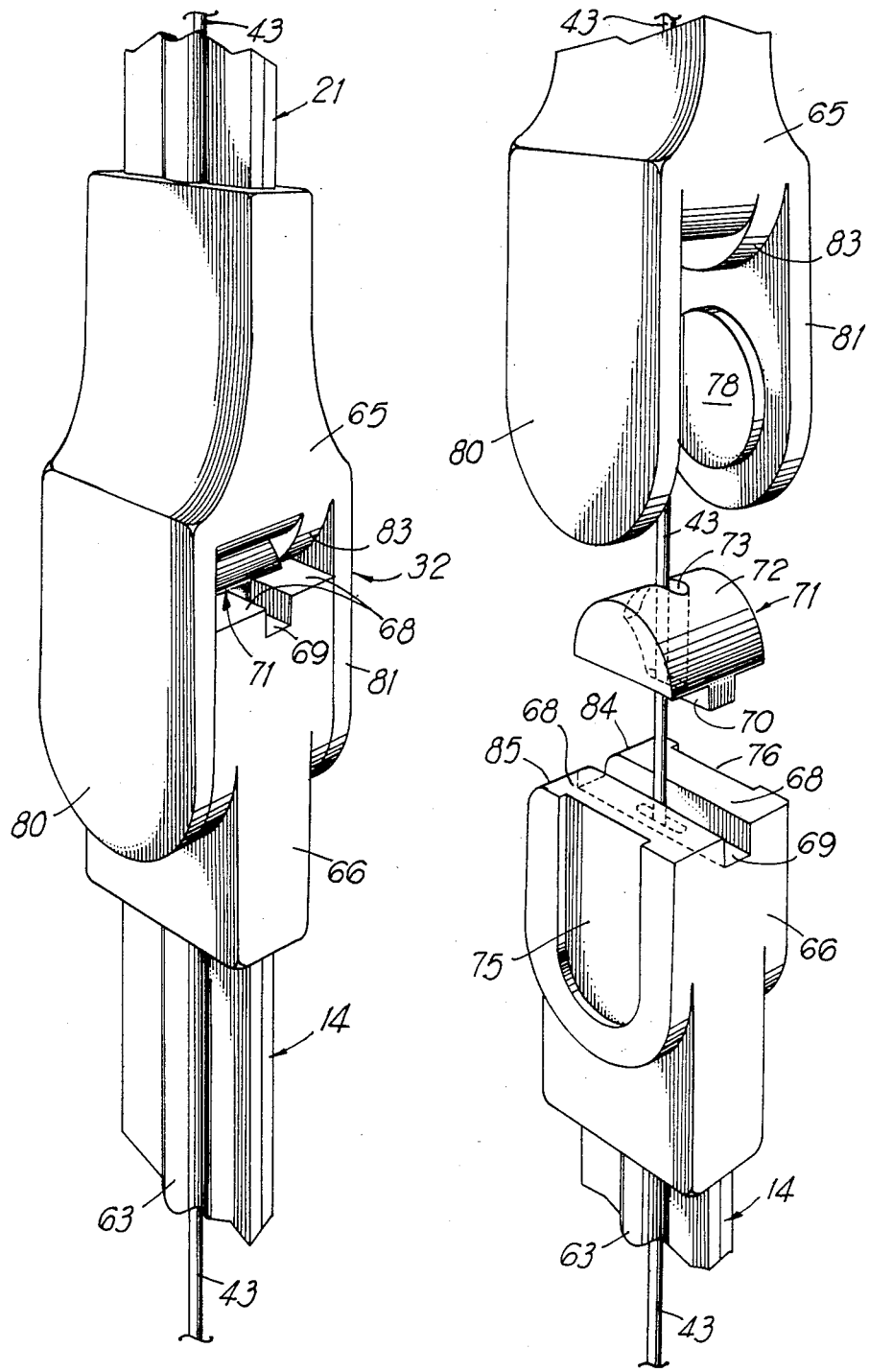
FIG. 2 is an enlarged perspective view of portions of upper and lower brace members connected by a knee joint.
FIG. 3 illustrates the components of FIG. 2 in exploded relation.

The construction of the knee joints 31 and 32 is probably best illustrated in FIGS. 2 and 3. As is shown in FIG. 3, the lower element 66 is provided with a top flat surface 68 interrupted by the slot or channel 69 which slot is adapted to receive the tongue 70 of the semicylindrical member indicated generally by the reference character 71. The member 71 presents a semicylindrical surface 72 and is provided with a generally fan-shaped slot 73 which receives the cable 43 or its equivalent therethrough, substantially as is shown in FIG. 3. The member 71 is adhesively secured to the upper portion of the member 66 by suitable adhesive material such as synthetic resin cured to effect the requisite bonding action of these two components together. The reason for the separate construction of the member 71 rather than integrally with the member 66 is to allow the cylindrical surface 72 to be positioned very accurately back and forth by sliding the tongue 70 in the groove 69 to fit the needs of an individual user. The opposite sides of the member 66 are provided with the side face recesses 75 and 76 which are adapted to receive the pivot bosses 77 and 78 (see also FIG. 5) which are mutually oppositely directed toward one another on the inner side of the depending leg portions 80 and 81 of the upper member 65. In addition to the boses 77 and 78, the inner sides of the legs 80 and 81 are provided with the cam surfaces 82 and 83 which are adapted to cooperate with the rounded cam corners 84 and 85 of the lower part 66 as will be more evident hereinafter when a further description of FIG. 4 is given. Between the cam surfaces 82 and 83, the juncture between the two legs 80 and 81 is formed as a saddle to present the arcuate surfaces 87 and 88 as shown in FIG. 4 which are adapted to seat upon the cylindrical surface 72 in full engagement therewith insofar as the full extents of the surfaces 87 and 88 are concerned. The two surfaces 87 and 88 are disposed on either side of the central channel 89 which passes the tensioning member 43 therethrough. When, however, the upper portion 65 is rotated with respect to the lower portion 66, the rounded corners 91 and 92 of the saddles are effective to allow the camming action illustrated by the various dashed line positions of the upper member 65 shown in FIG. 4. For example, the more the upper member 65 is rotated toward the right angular position with respect to the member 66, the rounded corner 92 becomes the only bearing point on the surface 72, the remainder of the saddle having been moved away as is clearly shown and, ultimately, the cam surfaces 82 and 83 engage their respective corners 84 and 85. The purpose of this camming action is to cause a relative sliding movement between the upper and lower portions 65 and 66. Thus, the bosses 77 and 78 ride upwardly within their recesses 75 and 76. This action may be to correspond accurately with the normal action of the user's knee.

Figure 11:
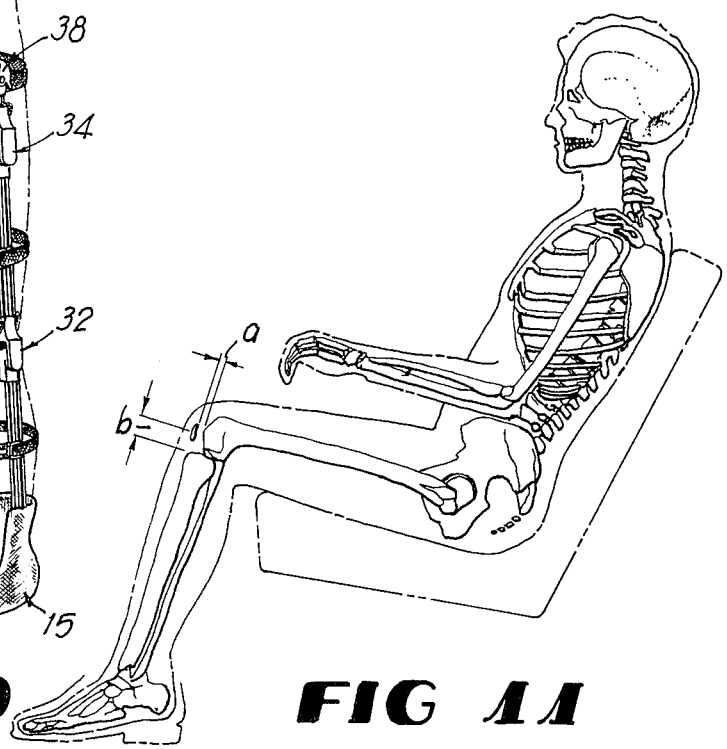
FIG. 11 is a diagrammatic view illustrating the need for sliding connection in the knee joint of the brace.
Figures 12, 13:
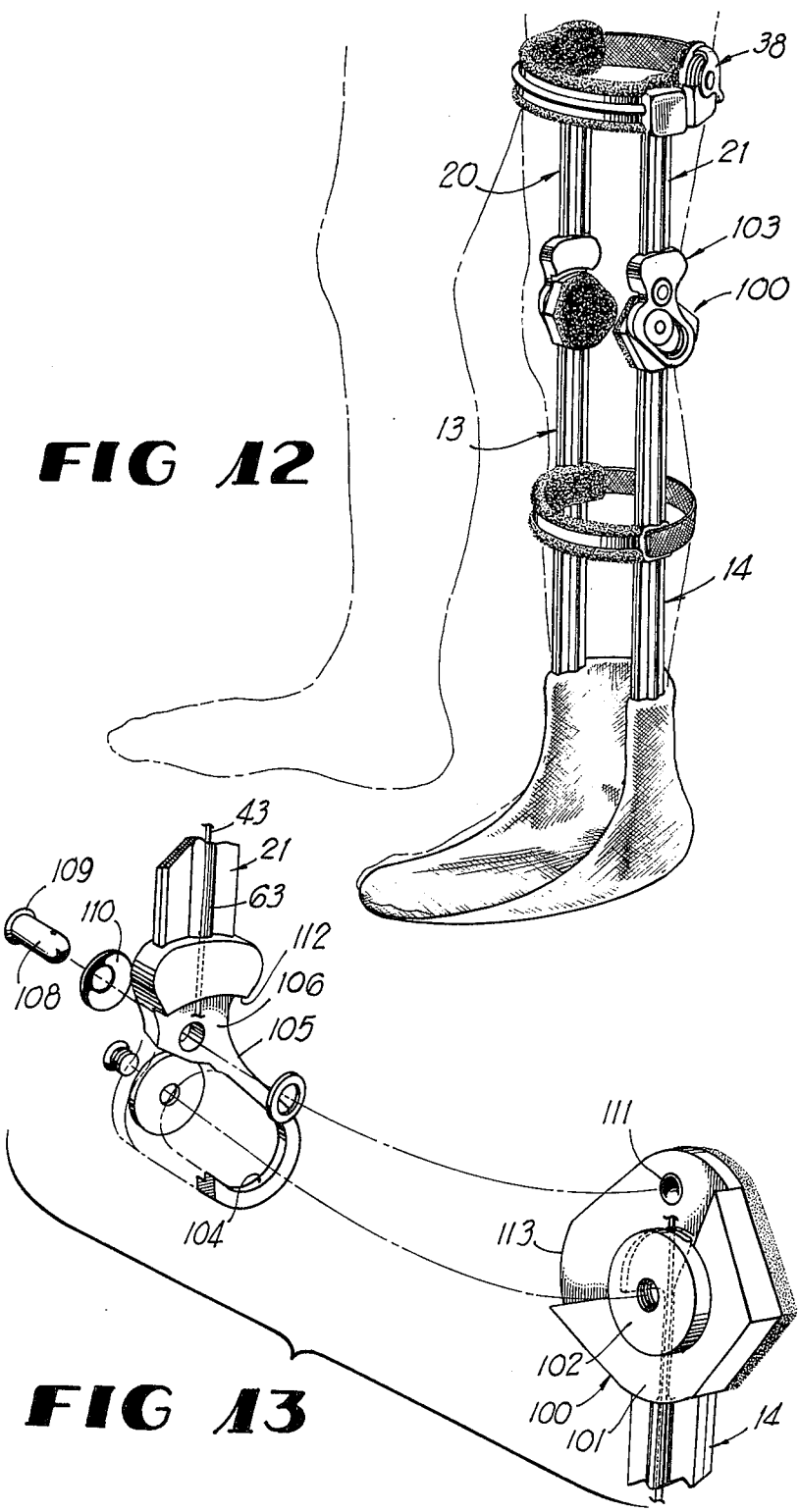
FIG. 12 is a perspective view of still another embodiment of the invention using a modified knee joint.
FIG. 13 is an exploded perspective view of the modified knee joint.

To illustrate this normal action, reference is had to FIG. 11 wherein the two distances a and b are shown. When the leg is flexed as shown in FIG. 11, the total distance a plus b has to be accommodated, the distance b being that to which the lower leg portion is extended relative to the upper leg portion and this is the extent to which the camming action must be applied to allow the lower brace members 13 and 14 to move away from, relatively, the upper brace members 20,21. When the user is standing upright or when the leg is extended, the distance b must be foreshortened as between the upper and lower brace members. The camming mechanism may be accurately constructed to accomodate precisely for the distance b for a particular user. This will assure that there is absolutely no stress or strain applied to the user's knee joint during flexion and extension of his leg and that the firmly anchored upper and lower braces will not tend to ride or creep along the user's skin such as might cause chafing or soreness. On the other hand, it is not essential that the exact duplication of the knee action be attained but, that sufficient sliding action be achieved as to alleviate any such tendencies. To aid in this application, it is appreciated that the springs such as 47 and 44 or the spring 54 will, when the tensioning means is relaxed, still have sufficient tension in them to easily allow accommodations for variations in motions as between the knee joint means and the actual normal action of the user's knee.

It will also be appreciate from FIG. 4 that when the knee joint component parts 65 and 66 are in the leg extended position as is shown in full lines in that Figure, an increased tension on the cable 43 will firmly frictionally interengage the component 71 in the arcuate saddle surfaces 87 and 88 of the upper member 66. This tends to rigidly unite the upper and lower brace portions so that the user's leg is stiffened despite the fact that significant muscle deterioration is present in the leg musculature. When the user desires to flex the leg, the pawl and ratchet mechanism 38 is released to decrease the tension on the cable 43 and thus allow relatively easy sliding motion between the portions 65 and 66 for flexing the leg.

Figure 8:
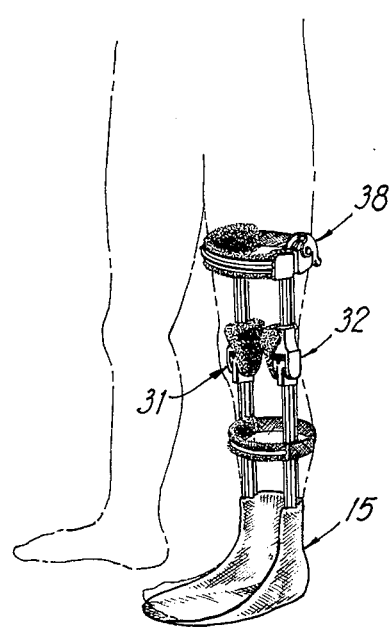
FIG. 8 is a perspective view of another embodiment of the invention.
Figure 9:
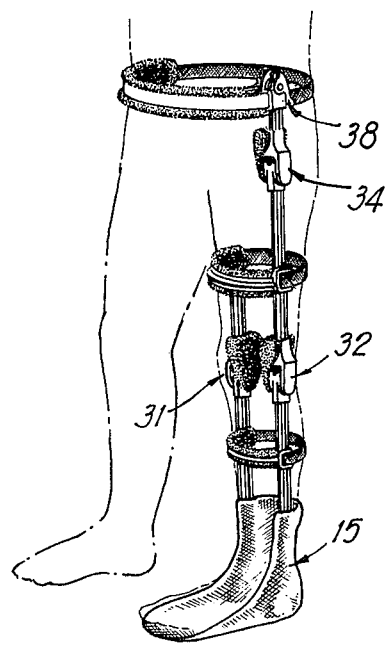
FIG. 9 is a perspective view similar to FIG. 1.
Figure 10:
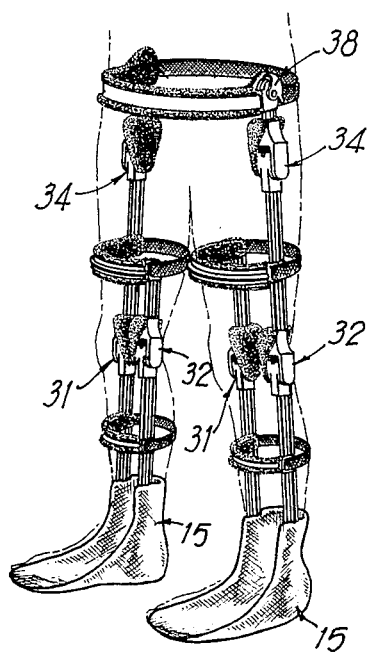
FIG. 10 is a perspective view of a further embodiment of the invention.

FIG. 9 shows the assembly of FIG. 1 whereas FIG. 8 shows a modified form of the invention wherein the hip joint and waist connector are not employed, the pawl and ratchet 38 then being located at the thigh connection as illustrated. Alternatively, a full orthopedic hip and knee brace for both legs may be utilized as is shown in FIG. 10, in which case there will be an individual pawl and ratchet 38 for each leg.

Insofar as the hip joints 34 of this invention are concerned, where used, they need not be of a sliding and pivoting type but merely provide a pivoting action and thus they may be identically constructed as is shown in FIGS. 2-7 except for the camming surfaces mentioned in connection therewith.

A modified form of knee joint means is illustrated in FIGS. 12-16. In this configuration, the lower member 100 of the knee joint means is provided on one side face 101 thereof with an outstanding circular boss 102 as can be seen best in FIG. 13. The upper knee joint means component 103 is provided with a portion having a downwardly angled, elongate opening or slot 104 which is adapted to receive the boss 102 to allow the pivotal and sliding connection requisite for the proper operation of the knee joint means. As can be seen best in FIG. 16, with the boss 102 received in the opening 104 of the downwardly angulated portion 105, and with the upper and lower knee joint components 103 and 100 in the leg extended position as shown in FIG. 16, the boss 102 is seated in the upper end of the slot or opening 104 and the two cut away faces 106 and 107 of the two components 100 and 103 provide a space therebetween through which the cable 43 passes as shown. The upper member 103 has a bore receiving a locking pin 108 whose head 109 bears against a Belleville type spring 110. The inner end of the pin 108 is provided with a bore therethrough which receives the cable 43 so that when the cable is tensioned to frictionally seat the boss 102 within the slot 104, the pin 108 is inwardly retracted from its dotted line position in FIG. 16 to the full line position therein wherein the head or inner end thereof 111 seats within a recessed or detent in the inner face 107 of the lower unit 100. This provides a positive locking action when the leg is in an extended position.

On the other hand, when the tensioning means is relaxed and the pin 108 is urged by the Belleville spring 110 to the dotted line position to unlock the two components 100 and 103, the user's leg may then be flexed to a position as is shown in FIG. 15. At this time, the two cam surfaces 112 and 113 come into play so as to cause the sliding action between the two knee joint means components 100 and 103 so that the boss 102 tends to travel towards the lower or opposite end of the opening 104.

As has been noted hereinbefore, either one of the cable systems shown in FIGS. 17 and 18 are possible. It will be noted that whereas the cable 43 passing between connecting points 45 and 48 through the two springs 44 and 47 and over the guide means 51 and 50 can, when the cable 42 is completely relaxed, establish a predetermined tension in the springs 44 and 47 which cannot be lessened. That is to say, the only action which can happen through the ring or loop 52 is that the spring tension in 44 and 47 can be equalized and increased to achieve the requisite locking or rigidifying action necessary. In the FIG. 18 embodiment, the minimum tension in the spring 54 is not so easily controlled.

Having now fully described the invention, it will be apparent to one of ordinary skill in the art that many modifications can be made thereto without departing from the spirit of scope of the invention as set forth herein.

What is claimed is:

1. In an orthopedic leg brace assembly, the combination of an elongated lower brace member and means or anchoring said lower brace member to the lower portion of the user's leg, a lower knee joint member engaged on the upper end of said lower brace member, an upper knee joint member slidably and pivotally engaged with said lower knee joint member, an elongate upper brace member engaged on said upper joint member and means for anchoring said upper brace member to the upper portion of a user's leg, passage means disposed in said brace members and said knee joint members, user-actuated tensioning means including a flexible tension member disposed in said passage means, and having an engaged position for drawing said knee joint means together and maintaining said brace members and said knee joint members locked in generally axial alignment, and a disengaged position for releasing said tension member for relative movement between said upper and lower knee joint members, and means for adjusting said tensioning means between engaged and disengaged positions.

2. In an orthopedic leg brace assembly as defined in claim 1 wherein said lower knee joint and said upper knee joint present arcuate, interengaged surfaces when aligned, said tension means acting to forcibly interengage these surfaces, and said passage means in said knee joint means beind disposed generally through the center of rotation of said knee joint means.

3. In an orthopedic leg brace assembly as defined in claim 1, and including hip joint means pivotally mounted between said tensioning means and said knee joint means for at least approximating the movement of a user's hip joint when the user's leg is flexed.

4. In a orthopedic leg brace assembly as defined in claim 3 in which said hip joint means includes passage means disposed generally centrally therethrough for receiving said tension member.

5. An orthopedic leg brace assembly comprising a first pair of stanchion-like side braces adapted to recieve the lower portion of a user's leg therebetween and having securing means for firmly anchoring them to a user's leg, a second pair of stanchion-like side braces adapted to receive the thigh portion of a user's leg therebetween and having securing means for firmly anchoring them to a user's thigh so that the side braces of the first and second pairs are generally aligned when the user's leg is straight, two knee joint means connecting the proximal ends of the side braces of the first and second pairs of slidably and pivotally interconnecting such proximal ends during flexion and extension of the user's leg, cable means threaded through said side braces and respective knee joint means for forcibly interengaging said knee joint means in generally axial alignment when a user's leg is extended, and user mainpulated means having locked and unlocked positions for tensing said cable means to draw said knee joint means together to form a rigid brace effect between said first and second pairs when in said locked position when a user's leg is extended and for releasing the lock on said cable means when in said unlocked position for decreasing the tension in said cable means to allow said knee joint means to at least approximate the normal action of a user's knee joint when a user's leg is flexed.

6. An orthopedic leg brace assembly as defined in claim 5 including a foot orthosis joining the distal ends of said first pair of side braces.

7. In an orthopedic leg brace assembly as defined in claim 5, and including hip joint means pivotally mounted between said user manipulated means and said knee joint means for at least approximating the movement of a user's hip joint when the user's leg is flexed.

8. In an orthopedic leg brace assembly as defined in claim 7 in which said hip joint means includes passage means disposed generally centrally therethrough for receiving said cable means.

9. An orthopedic leg brace assembly comprising a lower side brace having securing means for firmly anchoring said lower side brace to the side of a user's leg, an upper side brace having securing means for firmly anchoring said upper side brace to the side of a user's thigh, said upper and lower side braces having proximal ends and knee joint means for pivotally and slidably joining said proximal ends to allow said proximal ends to move toward and away from each other in at least an approximation of the normal movement of a user's knee during extension and flexion of a user's leg, continuous passage means disposed in said upper and lower braces and said knee joint means, said passage means in said knee joint means being generally centrally disposed therein, user actuated tensioning means disposed in said passage means for locking said knee joint means in axial alignment when a user's leg is extended, and cam means for moving the proximal end of said lower side brace away from the proximal end of said upper brace when a user's leg is flexed.

10. An orthopedic leg brace assembly as defined in claim 9 wherein said tensioning means includes a flexible member for connecting said lower side brace, said knee joint means and said upper side brace.

11. An orthopedic leg brace assembly as defined in claim 10 including locking means actuated by said tensioning means for locking said knee joint means when a user's leg is in extended position.

12. An orthopedic leg brace assembly comprising a first pair of stanchion-like side braces adapted to receive the lower portion of a user's leg therebetween, having upper securing means for firmly anchoring them to a user's leg and an ankle-foot orthosis joining the distal ends of said first pair of side braces, a second pair of stanchion-like side braces adapted to receive the thigh portion of a user's leg therebetween and having upper securing means for firmly anchoring them to a user's thigh so that the side braces of the first and second pairs are generally aligned when the user's leg is straight, two knee joint means connecting the proximal ends of the side braces of the first and second pairs for slidably and pivotally interconnecting such proximal ends during flexion and extension of the user's leg and having central passage means therethrough, flexible tension means threaded through said side braces and said passage means in said respective knee joint means for aligning and forcibly interengaging said knee joint means when a user's leg is extended, and user manipulated means for increasing the tension in said flexible tension means to align said knee joint means and to form a rigid brace effect between said first and second pairs when a user's leg is extended and for decreasing the tension in said flexible tension means to allow said knee joint means to at least approximate the normal action of a user's knee joint when a user's leg is flexed, said side braces being removable with respect to said upper securing means, said knee joint means and said orthosis so as easily to be unstrung from said flexible tension means and replaced with longer side braces to accommodate for growth of the user.

* * * * *